United States Patent
Cox et al.

(10) Patent No.: US 7,173,222 B2
(45) Date of Patent: Feb. 6, 2007

(54) AEROSOL GENERATOR HAVING TEMPERATURE CONTROLLED HEATING ZONE AND METHOD OF USE THEREOF

(75) Inventors: Kenneth A. Cox, Midlothian, VA (US); Walter A. Nichols, Chesterfield, VA (US); F. Murphy Sprinkel, Jr., Glen Allen, VA (US); Douglas D. McRae, Chesterfield, VA (US); William R. Sweeney, Richmond, VA (US)

(73) Assignee: Philip Morris USA Inc., Richmond, VA (US)

( * ) Notice: Subject to any disclaimer, the term of this patent is extended or adjusted under 35 U.S.C. 154(b) by 155 days.

(21) Appl. No.: 10/279,035

(22) Filed: Oct. 24, 2002

(65) Prior Publication Data

US 2003/0132219 A1 Jul. 17, 2003

Related U.S. Application Data

(63) Continuation of application No. 09/742,322, filed on Dec. 22, 2000, now Pat. No. 6,501,052.

(51) Int. Cl.
*A05B 1/02* (2006.01)

(52) U.S. Cl. ....................... 219/486; 219/497; 219/505; 392/480; 392/492; 128/200.14

(58) Field of Classification Search ................. 219/483, 219/486, 497, 499, 501, 505; 392/480, 492; 128/200.14, 200.22
See application file for complete search history.

(56) References Cited

U.S. PATENT DOCUMENTS

| | | |
|---|---|---|
| 2,896,856 A | 7/1959 | Kravits |
| 3,084,698 A | 4/1963 | Smith |

(Continued)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |
| EP | 0358114 A | 3/1990 |
| EP | 0642802 A2 | 5/1996 |
| EP | 0816084 | 1/1998 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |
| WO | 02/051468 | 7/2002 |
| WO | WO03/012565 | 3/2003 |

OTHER PUBLICATIONS

Barry, P.W. et al. "In Vitro Comparison of the Amount of Salbutamol Available for Inhalation From Different Formulations Used with Different Spacer Devices" Eur Respir J 1997; 10: 1345–1348.

(Continued)

*Primary Examiner*—Mark Paschall
(74) *Attorney, Agent, or Firm*—Buchanan Ingersoll & Rooney PC

(57) ABSTRACT

A temperature and flow rate controlled capillary aerosol generator includes two heating zones optionally separated by a region in which a pressure drop is induced. Power is metered or applied to the downstream, second zone to achieve a target resistance, and therefore a target temperature, while power is metered or applied to the upstream, first zone to achieve a target mass flow rate exiting the second zone. A target temperature is achieved in the second zone to generate an aerosol from the liquid flowing through the generator at the desired mass flow rate.

20 Claims, 8 Drawing Sheets

U.S. PATENT DOCUMENTS

| | | | |
|---|---|---|---|
| 3,157,179 A | 11/1964 | Paullus et al. | |
| 3,162,324 A | 12/1964 | Houser | |
| 3,431,393 A | 4/1969 | Katsuda | |
| 3,486,663 A | 12/1969 | Humphrey | |
| 3,658,059 A | 4/1972 | Steil | |
| 3,716,416 A | 2/1973 | Adlhart et al. | |
| 3,750,961 A | 8/1973 | Franz | |
| 3,789,190 A * | 1/1974 | Orosy et al. | 219/497 |
| 3,847,304 A | 11/1974 | Cohen | |
| 3,859,398 A | 1/1975 | Havstad | |
| 3,902,635 A | 9/1975 | Jinotti | |
| 3,903,883 A | 9/1975 | Pecina et al. | |
| 3,904,083 A | 9/1975 | Little | |
| 3,967,001 A | 6/1976 | Almaula et al. | |
| 3,987,941 A | 10/1976 | Blessing | |
| 3,993,246 A | 11/1976 | Erb et al. | |
| 4,042,153 A | 8/1977 | Callahan et al. | |
| 4,060,082 A | 11/1977 | Lindberg et al. | |
| 4,077,542 A | 3/1978 | Petterson | |
| 4,161,282 A | 7/1979 | Erb et al. | |
| 4,162,501 A | 7/1979 | Mitchell et al. | |
| 4,215,708 A | 8/1980 | Bron | |
| 4,231,492 A | 11/1980 | Rios | |
| 4,258,073 A | 3/1981 | Payne | |
| 4,261,356 A | 4/1981 | Turner et al. | |
| 4,289,003 A | 9/1981 | Yang | |
| 4,291,838 A | 9/1981 | Williams | |
| 4,303,083 A | 12/1981 | Burruss, Jr. | |
| 4,383,171 A | 5/1983 | Sinha et al. | |
| 4,391,308 A | 7/1983 | Steiner | |
| 4,395,303 A | 7/1983 | Weir | |
| 4,433,797 A | 2/1984 | Galia | |
| 4,471,892 A | 9/1984 | Coleman | |
| 4,512,341 A | 4/1985 | Lester | |
| 4,575,609 A | 3/1986 | Fassel et al. | |
| 4,627,432 A | 12/1986 | Newell et al. | |
| 4,649,911 A | 3/1987 | Knight et al. | |
| 4,682,010 A | 7/1987 | Drapeau et al. | |
| 4,695,625 A | 9/1987 | Macdonald | |
| 4,700,657 A | 10/1987 | Butland | |
| 4,730,111 A | 3/1988 | Vestal et al. | |
| 4,735,217 A | 4/1988 | Gerth et al. | |
| 4,744,932 A | 5/1988 | Browne | |
| 4,749,778 A | 6/1988 | Fukuzawa et al. | |
| 4,762,995 A | 8/1988 | Browner et al. | |
| 4,776,515 A | 10/1988 | Michalchik | |
| 4,790,305 A | 12/1988 | Zoltan et al. | |
| 4,811,731 A | 3/1989 | Newell et al. | |
| 4,819,625 A | 4/1989 | Howe | |
| 4,819,834 A | 4/1989 | Thiel | |
| 4,829,996 A | 5/1989 | Noakes et al. | |
| 4,837,260 A | 6/1989 | Sato et al. | |
| 4,848,374 A | 7/1989 | Chard et al. | |
| 4,871,115 A | 10/1989 | Hessey | |
| 4,871,623 A | 10/1989 | Hoopman et al. | |
| 4,877,989 A | 10/1989 | Drews et al. | |
| 4,911,157 A | 3/1990 | Miller | |
| 4,922,901 A | 5/1990 | Brooks et al. | |
| 4,926,852 A | 5/1990 | Zoltan et al. | |
| 4,935,624 A | 6/1990 | Henion et al. | |
| 4,941,483 A | 7/1990 | Ridings et al. | |
| 4,947,875 A | 8/1990 | Brooks et al. | |
| 4,974,754 A | 12/1990 | Wirz | |
| 4,978,837 A * | 12/1990 | Eggleston | 219/497 |
| 4,982,097 A | 1/1991 | Slivon et al. | |
| 4,992,206 A | 2/1991 | Waldrop | |
| 5,021,802 A | 6/1991 | Allred | |
| 5,044,565 A | 9/1991 | Alexander | |
| 5,056,511 A | 10/1991 | ronge | |
| 5,060,671 A | 10/1991 | Counts et al. | |
| 5,063,921 A | 11/1991 | Howe | |
| 5,096,092 A | 3/1992 | Devine | |
| 5,125,441 A | 6/1992 | Mette | |
| 5,133,343 A | 7/1992 | Johnson, IV et al. | |
| 5,134,993 A | 8/1992 | van der Linden et al. | |
| 5,135,009 A | 8/1992 | Müller et al. | |
| 5,144,962 A | 9/1992 | Counts et al. | |
| 5,151,827 A | 9/1992 | Ven et al. | |
| 5,178,305 A | 1/1993 | Keller | |
| 5,184,776 A | 2/1993 | Minier | |
| 5,217,004 A | 6/1993 | Blasnik et al. | |
| 5,226,441 A | 7/1993 | Dunmire et al. | |
| 5,228,444 A | 7/1993 | Burch | |
| 5,230,445 A | 7/1993 | Rusnak | |
| 5,231,983 A | 8/1993 | Matson et al. | |
| 5,259,370 A | 11/1993 | Howe | |
| 5,290,540 A | 3/1994 | Prince et al. | |
| 5,298,744 A | 3/1994 | Mimura et al. | |
| 5,299,565 A | 4/1994 | Brown | |
| 5,322,057 A | 6/1994 | Raabe et al. | |
| 5,327,915 A | 7/1994 | Porenski et al. | |
| 5,342,180 A | 8/1994 | Daoud | |
| 5,342,645 A | 8/1994 | Eisele et al. | |
| 5,349,946 A | 9/1994 | McComb | |
| 5,395,445 A | 3/1995 | Bohanan | |
| 5,421,489 A | 6/1995 | Holzner, Sr. et al. | |
| 5,462,597 A | 10/1995 | Jubran | |
| 5,474,059 A | 12/1995 | Cooper | |
| 5,515,842 A | 5/1996 | Ramseyer et al. | |
| 5,522,385 A | 6/1996 | Lloyd et al. | |
| 5,556,964 A | 9/1996 | Hofstraat et al. | |
| 5,564,442 A | 10/1996 | MacDonald et al. | |
| 5,565,677 A | 10/1996 | Wexler | |
| 5,575,929 A | 11/1996 | Yu et al. | |
| 5,585,045 A | 12/1996 | Heinonen et al. | |
| 5,617,844 A | 4/1997 | King | |
| 5,642,728 A | 7/1997 | Andersson et al. | |
| 5,674,860 A | 10/1997 | Carling et al. | |
| 5,682,874 A | 11/1997 | Grabenkort et al. | |
| 5,730,158 A | 3/1998 | Collins et al. | |
| 5,743,251 A * | 4/1998 | Howell et al. | 128/200.14 |
| 5,756,995 A | 5/1998 | Maswadeh et al. | |
| 5,765,724 A | 6/1998 | Amberg et al. | |
| 5,823,178 A | 10/1998 | Lloyd et al. | |
| 5,839,430 A | 11/1998 | Cama | |
| 5,855,202 A | 1/1999 | Andrade | |
| 5,856,671 A | 1/1999 | Henion et al. | |
| 5,863,652 A | 1/1999 | Matsumura et al. | |
| 5,869,133 A | 2/1999 | Anthony et al. | |
| 5,872,010 A | 2/1999 | Karger et al. | |
| 5,878,752 A | 3/1999 | Adams et al. | |
| 5,881,714 A | 3/1999 | Yokoi et al. | |
| 5,906,202 A | 5/1999 | Schuster et al. | |
| 5,914,122 A | 6/1999 | Otterbeck et al. | |
| 5,932,249 A | 8/1999 | Gruber et al. | |
| 5,932,315 A | 8/1999 | Lum et al. | |
| 5,934,272 A | 8/1999 | Lloyd et al. | |
| 5,934,273 A | 8/1999 | Andersson et al. | |
| 5,944,025 A | 8/1999 | Cook et al. | |
| 5,954,979 A | 9/1999 | Counts et al. | |
| 5,957,124 A | 9/1999 | Lloyd et al. | |
| 5,970,973 A | 10/1999 | Gonda et al. | |
| 5,970,974 A | 10/1999 | Van Der Linden et al. | |
| 5,978,548 A | 11/1999 | Holmstrand et al. | |
| 5,993,633 A | 11/1999 | Smith et al. | |
| 6,014,970 A | 1/2000 | Ivri et al. | |
| 6,029,657 A * | 2/2000 | Centurey | 128/200.22 |
| 6,053,176 A | 4/2000 | Adams et al. | |
| 6,054,032 A | 4/2000 | Haddad et al. | |
| 6,069,214 A | 5/2000 | McCormick et al. | |
| 6,069,219 A | 5/2000 | McCormick et al. | |

| | | |
|---|---|---|
| 6,070,575 A | 6/2000 | Gonda et al. |
| 6,071,428 A | 6/2000 | Franks et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,528,018 B1 | 3/2003 | Berndt |
| 2001/0032647 A1 | 10/2001 | Schuster et al. |

OTHER PUBLICATIONS

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20 No. 3, pp. 7477–7505, May–Jun. 1994.

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

Notification of Transmittal of Preliminary Examination Report for PCT/US01/45257 dated Nov. 25, 2002.

European Official Action dated Feb. 8, 2005 for EP 01 984 945.4A.

* cited by examiner

AEROSOL GENERATOR HAVING TEMPERATURE CONTROLLED HEATING ZONE AND METHOD OF USE THEREOF

This application is a continuation divisional of Application No. 09/742,322, filed on Dec. 22, 2000 now U.S. Pat. No. 6,501,052.

BACKGROUND OF THE INVENTION

1. Field of the Invention

The present invention relates generally to aerosol generators and, more particularly, to aerosol generators able to generate aerosols without compressed gas propellants and methods of making and using such aerosol generators.

2. Brief Description of the Related Art

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, distributing insecticides and delivering paint and lubricant.

Various techniques are known for generating aerosols. For example, U.S. Pat. Nos. 4,811,731 and 4,627,432 both disclose devices for administering medicaments to patients in which a capsule is pierced by a pin to release a medicament in powder form. A user then inhales the released medicament through an opening in the device. While such devices may be acceptable for use in delivering medicaments in powder form, they are not suited to delivering medicaments in liquid form. The devices are also, of course, not well-suited to delivery of medicaments to persons who might have difficulty in generating a sufficient flow of air through the device to properly inhale the medicaments, such as asthma sufferers. The devices are also not suited for delivery of materials in applications other than medicament delivery.

Another well-known technique for generating an aerosol involves the use of a manually operated pump which draws liquid from a reservoir and forces it through a small nozzle opening to form a fine spray. A disadvantage of such aerosol generators, at least in medicament delivery applications, is the difficulty of properly synchronizing inhalation with pumping. More importantly, however, because such aerosol generators tend to produce particles of large size, their use as inhalers is compromised because large particles tend to not penetrate deep into the lungs.

One of the more popular techniques for generating an aerosol including liquid or powder particles involves the use of a compressed propellant, often containing a chlorofluoro-carbon (CFC) or methylchloroform, to entrain a material, usually by the Venturi principle. For example, inhalers containing compressed propellants such as compressed gas for entraining a medicament are often operated by depressing a button to release a short charge of the compressed propellant. The propellant entrains the medicament as the propellant flows over a reservoir of the medicament so that the propellant and the medicament can be inhaled by the user.

In propellant-based arrangements, however, a medicament may not be properly delivered to the patient's lungs when it is necessary for the user to time the depression of an actuator such as a button with inhalation. Moreover, aerosols generated by propellant-based arrangements may have particles that are too large to ensure efficient and consistent deep lung penetration. Although propellant-based aerosol generators have wide application for uses such as antiperspirant and deodorant sprays and spray paint, their use is often limited because of the well-known adverse environmental effects of CFC's and methylchloroform, which are among the most popular propellants used in aerosol generators of this type.

In drug delivery applications, it is typically desirable to provide an aerosol having average mass median particle diameters of less than 2 microns to facilitate deep lung penetration. Most known aerosol generators are incapable of generating aerosols having average mass median particle diameters less than 2 microns. It is also desirable, in certain drug delivery applications, to deliver medicaments at high flow rates, e.g., above 1 milligram per second. Most known aerosol generators suited for drug delivery are incapable of delivering such high flow rates in the 0.2 to 2.0 micron size range.

U.S. Pat. No. 5,743,251, which is hereby incorporated by reference in its entirety, discloses an aerosol generator, along with certain principles of operation and materials used in an aerosol generator, as well as a method of producing an aerosol, and an aerosol. The aerosol generator disclosed according to the '251 patent is a significant improvement over earlier aerosol generators, such as those used as inhaler devices. It is desirable to produce an aerosol generator that is portable and easy to use.

SUMMARY OF THE INVENTION

The invention provides a capillary aerosol generator comprising a flow passage having an inlet, an outlet, a first heater in heat transfer communication with a first zone of the flow passage adjacent the inlet, a second heater in heat transfer communication with a second zone of the flow passage adjacent the outlet, and an optional flow constriction in the flow passage between the first zone and the second zone.

The invention also provides a process of forming an aerosol from a liquid, comprising the steps of supplying pressurized liquid to an upstream end of a flow passage of an aerosol generator including a first heater positioned in heat transfer communication with a first zone of the flow passage, a second heater positioned in heat transfer communication with a second zone of the flow passage and an optional flow constrictor in the flow passage between the first zone and the second zone; measuring a parameter indicative of the mass flow rate of the fluid flowing through the second zone; changing the temperature in the first zone based on the measurement of the mass flow rate of the fluid through the second zone; and heating the liquid in the second zone such that the liquid is volatilized and after exiting from a downstream end of the flow passage forms an aerosol.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now described in more detail with reference to preferred embodiments of the apparatus and method, given only by way of example, and with reference to the accompanying drawings, in which.

DESCRIPTION OF THE PREFERRED EMBODIMENTS

When referring to the drawing figures, like reference numerals designate identical or corresponding elements throughout the several figures.

According to one aspect of the present invention, a capillary aerosol generator incorporates two heated zones. Each zone is heated by applying a voltage across a resistive element. The resistive elements may be film heaters, such as Pt heaters, applied to a supporting structure through which the fluid flows, e.g., flow chambers such as cylindrical or rectangular flow passages incorporating the film heaters. Fluid can be supplied to the generator, preferably at a substantially constant pressure, from a fluid source upstream of the generator. Alternatively, the fluid can be supplied at constant linear displacement rate by a syringe pump. The purpose of the second zone is to vaporize the fluid as it is transported through the tube and after exiting the tube forms an aerosol. Temperature in either heating zone can be measured directly by thermocouples or calculated based on measurement of a parameter such as the resistance of the heating element.

The resistive heating element of the second zone has a suitable temperature coefficient (positive or negative) of resistance, which is preferably a high coefficient of resistance. The second zone is heated by the application of power to the resistive element while the resistance across the element is monitored. The monitored resistance can provide an indication of the temperature of the heating element because the resistance of the heating element varies as a function of its temperature. For example, if the resistance heater is made of platinum, the temperature coefficient of resistance of platinum is $0.00392$ $(° C.)^{-1}$. Using the relationship $R=R_0[1+\alpha(T-T_0)]$, which defines the resistance value R where $R_0$ is the resistance at Temperature $T_0$ and T is the temperature for which R is calculated, a platinum heater having a resistance of 5 ohms at 0° C., the resistance of the heater will vary linearly from about 0.55 ohms at 20° C. to about 0.9 at 200° C. Thus, by controlling power to a target resistance, the heater can be maintained at a precise target temperature and thereby minimize the possibility pf thermally degrading the fluid or fluids being heated.

The resistance of the second zone's heater element can be fed back in a control scheme to meter power to the second zone, so that by metering the power to the second zone a target resistance of the second zone heater element is achieved, and therefore the average temperature of the second zone's heater element can be maintained at a target value. At the same time, the power supplied to the second heater element is measured. This power usage data is a measure of the mass flow rate of liquid to and through the second zone, and therefore through the generator as a whole. In this way, power monitoring at the second zone serves as a mass flow meter of the fluid flowing through the generator.

According to another aspect of the invention, it is possible to control an aerosol generator to deliver a target total mass (e.g., a dose) of volatilized fluid. In particular, a multi-zone heating arrangement in accordance with the invention can provide a mass flow rate through the heating arrangement which is proportional to the power usage of the heating arrangement. Further, with such a heating arrangement, a total mass (e.g., dose) can be made to be proportional to the total energy used by the heating arrangement. In a medical inhaler, control of the actual dose can be obtained by controlling the fluid flow rate based on a target power level which can be achieved by timing the period of power supply to attain the desired total energy level. Alternatively, a target total energy level can be selected and the fluid flow rate can be adjusted to achieve that target energy level in a present time.

As discussed briefly above, constant pressure fluid is preferably supplied to the upstream, first zone of the generator. The rate at which liquid is delivered from the first heating zone to the second heating zone is dependent upon the pressure drop across the entire fluid channel downstream of the pressure source. According to yet another aspect of the present invention, a segment of small bore tubing, a porous pressure drop element, or other element which functions to throttle fluid flow, is positioned between the outlet of the first zone and the inlet of the second zone. The pressure drop across this element is designed to be a large fraction of the pressure drop across the entire fluid channel downstream of the pressure source and is a function of or depends upon the viscosity of the liquid, which in turn depends upon the temperature of the fluid. The application of power to the first zone is controlled to control this temperature and thus the liquid flow rate through the first zone. Power applied to the first zone is controlled to achieve a target power usage in the downstream, second zone, required to maintain the second zone's heater element at a target temperature. In this manner, power control in the first zone serves as a mass flow controller of fluid flowing through both of the first and second zones and therefore the generator as a whole.

The feedback control scheme implemented is designed so that a target flow rate through the generator is achieved when the temperature of the liquid exiting the first zone is at a target temperature above the highest anticipated ambient temperature in which the generator would be used. In this way, the mass flow rate can be controlled to its target value independent of ambient temperature and independent of the pressure applied to the liquid, because the temperature of the liquid entering the second zone is substantially the same across a wide range of ambient environmental temperatures and because the source of fluid supplies the fluid at a substantially constant pressure. A generator according to the present invention therefore is capable of reducing the likelihood of overheating the liquid, and controlling the aerosol delivery rate in the presence of variations in ambient temperature and pressure applied to the liquid.

One object of the present invention is to provide controlled heating along the length of the capillary tube used to heat and vaporize a flowing liquid inside the tube. There are numerous benefits which can be achieved through the use of this approach to heating. As overheating the fluid is not desirable and if sections of the tube walls become too hot due to localized vaporization or bubbles in the liquid stream, the liquid materials may be thermally degraded. The present invention instead provides multiple heated areas which can be easily monitored and readily react to a control scheme. Furthermore, a generator according to the present invention is thus capable of compensating for materials which are not delivered to the tube at optimum temperatures. Further, a generator according to the present invention is capable of reacting to or accommodating changes in flow rates and liquid density inside the tube after the fluid has been introduced into the generator, and the several heating segments can actively respond to the output of sensors independent of the other segments.

According to a first exemplary embodiment, a capillary aerosol generator comprises a capillary tube having a inlet port, an outlet port, and a lumen extending through the tube from the inlet port to the outlet port, a first heater in heat transfer communication with a first zone of the tube adjacent to the inlet port, a second heater in heat transfer communication with a second zone of the tube adjacent to the outlet port, a flow constriction in the tube lumen between the first zone and the second zone.

According to a second exemplary embodiment, a process of forming an aerosol from a liquid comprises the steps of providing an aerosol generator including a tube, a first heater positioned in heat transfer communication with a first, upstream zone of the tube, a second heater positioned in heat transfer communication with a second, downstream zone of the tube, and a flow constrictor in the tube between the first zone and the second zone, supplying the liquid at a pressure to an upstream end of the tube, measuring a characteristic of the tube indicative of the mass flow rate of the fluid flowing through the tube in the second zone, changing the temperature of the tube in the first zone based on the measurement of the mass flow rate of the fluid through the second zone, and allowing the liquid to exit the tube at a downstream end of the tube.

In developing capillary aerosol generators it is desirable to improve control of the rate at which liquid is introduced into the capillary tube and the rate at which power is metered to the capillary tube's heater. Failure to correctly control these parameters can result in overheating of the liquid, resulting in thermal degradation of the liquid material and subsequent clogging of the capillary by the byproducts of this thermal degradation.

Figure 3:
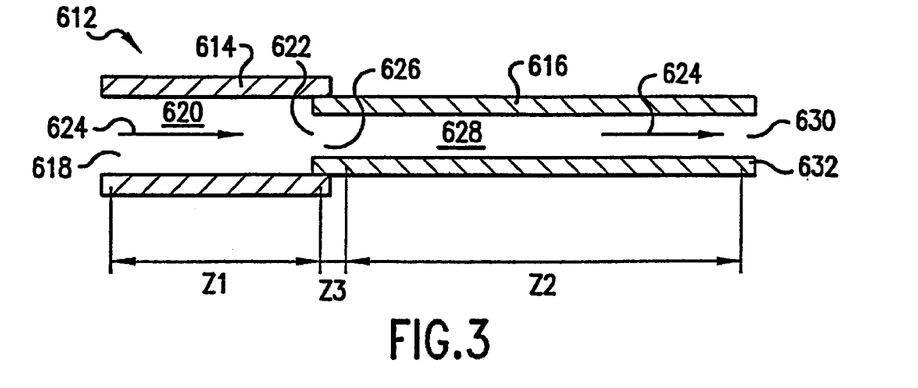
FIG. 3 schematically illustrates another embodiment of a portion of the CAG illustrated in FIG. 2.

One aspect of the present invention is the reduction in the likelihood that the liquid in the capillary tube is improperly heated, by controlling the energy supplied to a liquid vaporization zone (a downstream, second heating zone) to achieve a target temperature, while controlling the energy supplied or power metered to a liquid flow rate control zone (an upstream, first zone) to achieve the target liquid flow rate emerging from the aerosol generator. The capillary aerosol generator according to the present invention includes heating elements and associated control circuitry which function as heating elements as well as flow meters and flow controllers.

According to a preferred embodiment, the present invention provides a capillary aerosol generator which includes a system for heating an essentially hollow, tubular structure using a series of heated zones to allow for different temperatures and rates of heating along the length of the tubular structure. The system includes a series of discrete heating elements along the length of the structure, or alternative arrangement such as by segmenting a continuous resistive heater using independent contacts along the length of the resistor. The resistive array of single resistive elements can have purposeful spacing between the heated sections and incorporate current, voltage, and/or temperature sensing devices along the tube length that can passively sense or be part of an active control system. The control system activates the individual heaters with a sequence of currents, voltages, or both, which delivers electrical power to the tube. Additionally, the control system can interact with and react to one or more of the sensors. Alternatively, the heaters can be inductive heaters instead of resistive heaters. The heater materials can be an integral part of the tube's walls or independent elements added to the structure.

FIG. 1 shows an inhaler 500 incorporating a multi-zone heater 510 in accordance with the invention. The inhaler 500 includes a first housing 520 having a mouthpiece 522 and second housing 530 which includes power source and logic circuitry as discussed in copending application Ser. No. 09/172,023, filed Oct. 14, 1998, the disclosure of which is hereby incorporated by reference. An aerosol is generated by a heated tube 540 incorporating the multi-zone heater 510. Liquid from a pressurized source 550 passes through a valve 560 and into a first heated zone Z1 of the tube 540 and the vapor is generated in a second zone Z2 of the tube 540. The vapor mixes with air inside the housing 520 to form an aerosol and the resulting mixture can be inhaled through the mouthpiece 522.

FIG. 2 schematically illustrates an exemplary capillary aerosol generator (CAG) system 600 in accordance with the present invention. CAG system 600 includes a source of pressurized fluid 604, a CAG 602, and a valve 606. Valve 606 controls the flow of pressurized fluid from source 604 to CAG 602, and can be controlled either manually or, more preferably, under control of a controller, as described in greater detail below. A controller 608 is also provided for controlling the operation of CAG 602, and optionally also controls valve 606. Valve 606 can alternatively be controlled by a separate controller (not illustrated).

CAG 602 is divided into at least two heating zones: an upstream, first zone Z1; and a downstream, second zone Z2. The two zones can be optionally separated by an intermediate zone Z3. Each of zones Z1, Z2 includes an electrical heating element which heats up upon the application of a voltage across and current through the heating element, as will be readily appreciated by one of ordinary skill in the art. Controller 608 is placed in electrical communication with and across both zones Z1 and Z2, as illustrated in FIG. 2, and selectively applies voltage across and current through the heaters in the zones. Controller 608 can be provided with a memory 610 in which an instruction set for operation of the controller can be stored. Controller 608 can be a general purpose digital computer which operates under software control, the set of software instructions being stored in volatile or non-volatile memory 610, or optionally and alternatively controller 608 can be a specially constructed, expert controller including discrete digital or analog components which together embody the instruction set for controller 608. As the specific construction of controller 608 will be readily appreciated by one of ordinary skill in the art upon a complete reading of the descriptions herein, no further description of the specific design of controller 608 will be undertaken.

FIG. 3 illustrates another embodiment of a CAG in accordance with the present invention, GAG 612. GAG 612 includes a first, upstream tube 614 and a second, downstream tube 616. First tube 614 includes a proximal inlet 618, a flow passage 620, and a distal outlet 622. Inlet 618 is in fluid communication with source 604, as described above, and directs a fluid, preferably a liquid, along a fluid flowpath 624 downstream to outlet 622. Second tube 616 is positioned downstream of outlet 622, and includes a proximal inlet 626, a flow passage 628, and a distal outlet 630. As illustrated in FIG. 3, first tube 614 has a fluid flow cross section which is greater than the fluid flow cross section of second tube 616, and inlet 626 is positioned at outlet 622, i.e., there are no structures between inlet 626 and outlet 622.

First tube 614 and second tube 616 include a heater element or elements therein or thereon to which controller 608 is electrically connected. The heaters can be made integral with the tubes, such as by forming the tubes themselves of a material which is sufficiently electrically resistive to act as an electrical heater for the fluid contents of the tube. Alternatively, tubes 614, 616 can include one or more internal or external heaters mounted to the tubes which heat when a voltage is applied to them, and which in turn heat the tubes and their fluid contents. Controller 608, in accordance with the instruction set contained in memory 610 or the logic of its discrete elements, selectively applies a voltage to the heater associated with one or both of tubes 614, 616. The voltage applied causes the heater element(s) to increase in temperature, which in turn heats the fluid contents of the respective tube by convection and/or conduction. As described in greater detail herein, one or both of tubes 614, 616 and their fluid contents can be selectively heated. At the same time, a parameter such as resistance of the heater element heating the tube 614 can be measured to monitor the temperature of the tube 616 and the power used to heat the tube 616 can be measured to determine the mass flow rate of fluid flowing through the CAG.

As outlet 630 is the port from which vaporized fluid exits CAG 612, it is preferable that outlet 630 is unobstructed so that the flow of fluid out of CAG 612 is not impeded at outlet 630. Furthermore, by providing a zone of reduced cross section downstream of the first tube 614, a throttle is formed which induces a pressure drop. This optional throttle or other constriction which causes a drop in fluid pressure in CAG 612 is located downstream of first tube 614 and is substantially confined to zone Z3 (see FIG. 2). By forming a structure in CAG 612 which induces or causes a drop in fluid pressure in the flow passages of tubes 614, 616, it is possible to control the mass flow rate of fluid flowing through the CAG. It is therefore preferable that tubes 614, 616 include no or substantially no source of a reduction in fluid pressure along their lengths, so that the mass flow rate of fluid through the CAG can be determined and maintained at a desired level by controller 608.

Figure 1:
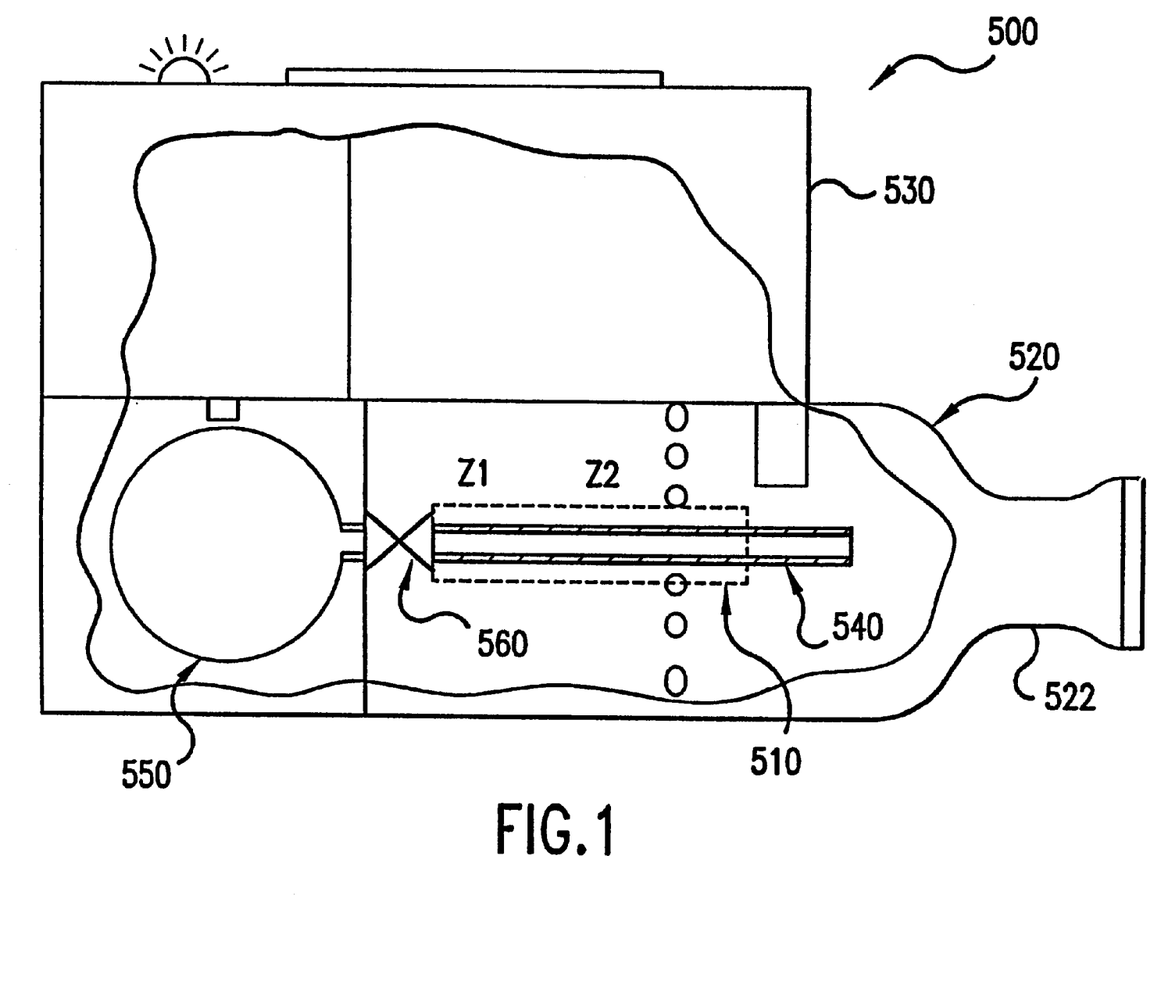
FIG. 1 schematically illustrates an inhaler incorporating a multi-zone heating apparatus in accordance with the invention.
Figure 2:
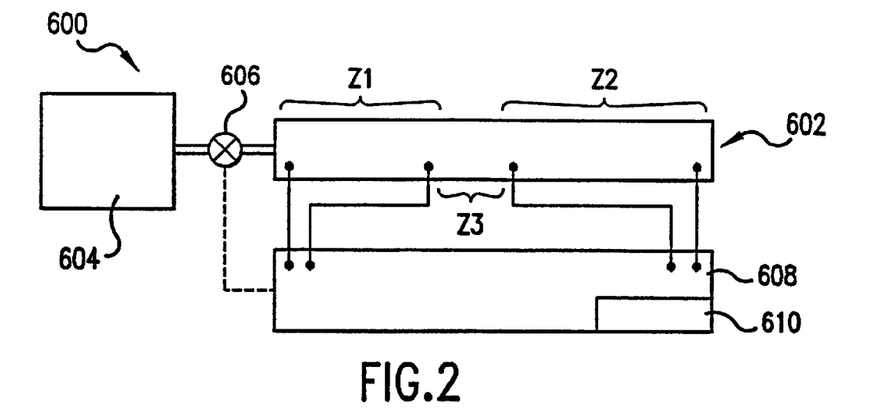
FIG. 2 schematically illustrates an exemplary capillary aerosol generator (CAG) system in accordance with the present invention.

FIG. 2 and FIG. 3 illustrates that controller 608 is electrically connected to first tube 614 to define first zone Z1, and electrically connected to second tube 616 to define second zone Z2. GAG 612, as with other embodiments of GAG 602 described herein, may optionally include a temperature sensing device 632 attached to or formed in the distal end of second tube 616. Temperature sensor 632 can be a thermistor or other temperature sensitive device which can provide a signal which includes data representative of the temperature of the distal end of second tube 616. Temperature sensor 632 can be in electrical communication with controller 608 so as to provide a signal indicative of the temperature of the distal end of second tube 616 to the controller to provide a feedback signal for controlling the application of power to first tube 614, second tube 616, or both, as described in greater detail below.

Figure 4:
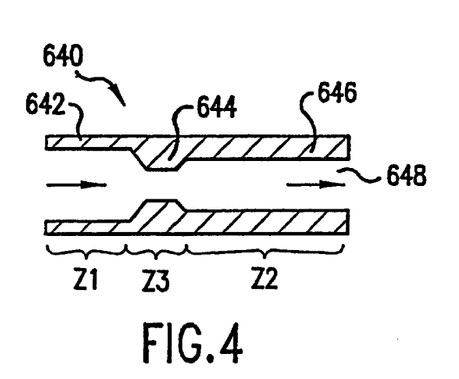
FIG. 4 schematically illustrates another embodiment of a portion of the CAG illustrated in FIG. 2.

Turning now to FIG. 4, yet another embodiment of CAG 602, CAG 640, is illustrated. CAG 640 is similar in many respects to CAG 612, except that CAG 640 is formed as a monolithic, integral, unitary structure formed as a single piece. A first, proximal, upstream portion 642 receives pressurized fluid from source 604, as described above. An optional flow constrictor 644 is formed distally downstream of portion 642, and creates a drop in fluid pressure. A second, distal portion 646 is formed downstream of constrictor 644, and includes a distal exit port 648 from which vaporized fluid exits CAG 640. Thus, zone Z1 includes portion 642, zone Z2 includes portion 646, and zone Z3 includes constrictor 644. As in CAG 612, the heater elements for each of portions 642, 646 can be a portion of the walls of the CAG, attached to the walls of the CAG, or combinations thereof.

Figure 5:
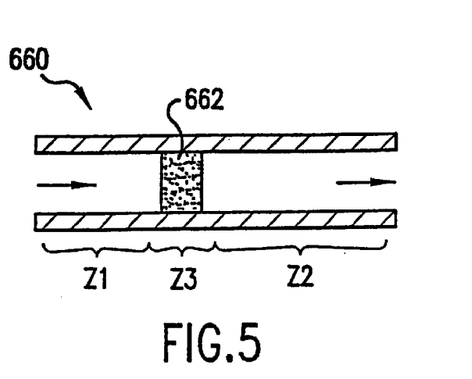
FIG. 5 schematically illustrates another embodiment of a portion of the CAG illustrated in FIG. 2.

FIG. 5 schematically illustrates yet another embodiment, CAG 660. Similar to CAG 640, CAG 660 is preferably formed from a single piece of material and is electrically connected to controller 608 to define zones Z1, Z2, and Z3, as described above. Different from CAGs 612, 640, CAG 660 has a constant internal flow cross-sectional area in zones Z1 and Z2, and an optional constrictor 662 is mounted or otherwise provided in zone Z3 to cause a drop in fluid pressure. Preferably, constrictor 662 is a porous plug formed of a material non-reactive to the fluid intended to flow through CAG 660, and includes pores therein which allow the fluid to flow through the plug and the CAG. Constrictor 660 is designed to provide a drop in fluid pressure between zones Z1 and Z2 at a predetermined fluid pressure and viscosity, in a manner well appreciated by one of ordinary skill in the art.

The function of controller 608 with CAG 612, 640, or 660 will now be described with reference to FIG. 6. Throughout this description, several variables will be discussed, as follows:

V(Z1)... voltage across zone Z1

V(Z2)... voltage across zone Z2

P(Z1)... electrical power used in zone Z1

P(Z2)... electrical power used in zone Z2

T(Z1)... average temperature of CAG in zone Z1

T(Z2)... average temperature of CAG in zone Z2

T (Z3)... average temperature of CAG in zone Z3

T(Z2')... temperature of CAG at distal end of zone Z2 r(Z1)... electrical resistance of portion of CAG in zone Z1 r(Z2)... electrical resistance of portion of CAG in zone Z2

M... mass flow rate of fluid

M(Z1)... mass flow rate of fluid flowing through zone Z1

M(Z2)... mass flow rate of fluid flowing through zone Z2 pr(Z1)... fluid pressure drop across zone Z1 pr(Z2)... fluid pressure drop across zone Z2 pr(Z3)... fluid pressure drop across zone Z3

η... fluid viscosity

From the foregoing description, because there is no loss of fluid in the CAG between zones Z1 and Z2, the mass flow rates through these zones are identical, or $$M(Z1)=M(Z2)=M$$

As well appreciated by one of ordinary skill in the art, the electrical power (P) of an electrical component, its resistivity (r), the current (i) flowing through the element, and the electrical potential or voltage (V) across the element are interrelated, according to well-known relationships:

$$V = ir$$

$$P = i^2 r$$

$$P = iV$$

$$P = V^2/r$$

Additionally, because of the design of the CAGs of the present invention, several other relationships can be used to measure and control electrical and physical characteristics of the CAG and the fluid flowing therethrough. It has been found by the inventors herein that the power consumed by the portion of the CAG in zone Z2 to maintain that portion of the CAG at a known temperature (the boiling point for the liquid being aerosolized, for example) is a function of the mass flow rate through the CAG:

$$P(Z2) = F(M)$$

The exact functional relationship between power and mass flow rate can be readily empirically determined, as will be readily apparent to one of ordinary skill in the art. Once this functional relationship is determined, it is used to form the instruction set in memory 610, or to design the logic of controller 608, as described below.

The materials from which the CAGs are formed, along with the heater elements themselves, are selected so that the average temperatures of zones Z1 and Z2 are functions of the resistance of the portions of the CAGs which are in these zones:

$$T(Z1)=F(r(Z1))$$

and $$T(Z2)=F(r(Z2))$$

Many materials, e.g., copper, stainless steel, and platinum, exhibit this relationship between temperature and resistance, and the function is linear over a wide range of temperatures. Thus, the material out of which the CAGs are formed, or at least the heater elements, is preferably selected to have a temperature-resistance function which is well known, and preferably linear, over the range of temperatures in which system 600 will be used and the fluid will be aerosolized at least in the case where the resistance of the heater element is used to measure the temperature of the tube.

The CAG is preferably designed so that when controller 608 attempts to maintain the power consumed by the portion of the CAG in zone Z2 at its target level, P (target), the temperature of zone Z1 will be at a level, which is preferably at or slightly above the highest ambient temperature at which it is anticipated that system 600 would be used.

Additionally, the fluid to be aerosolized is preferably delivered to zone Z1 by applying a constant pressure P. The fluid pressure drops across zones Z1 and Z2 are preferably close to zero:

$$pr(Z1)\approx pr(Z2)\sim 0$$

in which case:

$$P\approx pr(Z3)$$

Furthermore, the pressure drop across zone Z3 is related to the mass flow rate of the fluid flowing through the CAG and the viscosity, eta, of the fluid in zone Z3, according to the relationship:

$$pr(Z3)=k*M/eta$$

where k is a constant dependent upon the geometry of the channel in zone (Z3) and eta is the viscosity of the fluid in this zone, which viscosity is a function of the temperature of the fluid, that is:

$$eta=F(T(Z3))$$

Therefore:

$$P\sim k*M/eta$$

or $$M\sim P*eta/k$$

Thus, the mass flow rate of fluid through the CAG is determined by the applied pressure and the viscosity of the fluid in zone Z3. This latter quantity is, in turn, controlled by the temperature in zone Z3. It is for this reason that the flow constrictor is preferably provided, i.e., so that the mass flow rate can be more accurately controlled by adjusting the temperature in zone Z3.

These several functional interrelationships having been established, an examplary control scheme for controller 608 will now be described with reference to FIG. 6. At the initiation of a cycle of generating a predetermined amount or bolus of aerosolized liquid, valve 606 is opened, allowing liquid at a known and preferably constant pressure to enter the CAG. At step 700, controller 608 applies and controls voltages across Z1 and Z2 to raise the temperature of the fluid therein. At step 702, the controller measures resistance r(Z2), to measure T(Z2). Alternatively, or as a redundant measurement, the controller measures T(Z2') at step 704 at the exit of zone Z2 with the thermocouple or thermistor. At step 706, the controller then compares the measured value of T(Z2), and adjusts V(Z2), and therefore P(Z2), to achieve a measured, target r(Z2), and therefore a target T(Z2). As will be readily appreciated by one of ordinary skill in the art, the temperature achieved can be within a predetermined range and still satisfy this condition, i.e., a certain, predetermined error is acceptable.

The controller then measures P(Z2) at step 708 which was needed to maintain T(Z2) at (or acceptably near) the target value, which gives a measure of the mass flow rate M of fluid flowing through the CAG, as discussed above. At step 710, the controller evaluates if the power measured to maintain the proper temperature, P(Z2), is greater than the power necessary, P(target), from the empirical relationship between power and mass flow rate. If so, the controller decreases the voltage, and therefore the power, applied to zone Z1. This is because when the mass flow rate is higher than desired, the fluid flowing through the CAG will cool the zone Z2, requiring additional power to heat zone Z2 to the target temperature. A decrease in the voltage applied across zone Z1 lowers the temperature of the fluid therein, and therefore raises the viscosity, and therefore lowers the mass flow rate through zone Z2. This has the effect of making zone Z1 a flow controller for the CAG, and making zone Z2 a flow monitor for the CAG. Similarly, at step 712 if the power measured across zone Z2 to achieve the target temperature T(Z2) is less than the target power, the controller increases the voltage across (and therefore the power used by) zone Z1 to increase the temperature of the fluid flowing through zone Z1, and thereby raises the mass flow rate.

At step 714, the controller sums or integrates mass flow rate over time to determine the total mass (m) delivered during the cycle. At step 716, the total mass m delivered is compared with a predetermined desired value of m. If the total mass actually delivered is less than the amount desired to be delivered, then the controller returns to step 700. If the total mass delivered is equal to or greater than the total mass desired, the flow of fluid from the source 604 is terminated by valve 606, and the voltage(s) across zones Z1 and Z2 are set to zero.

Figure 6:
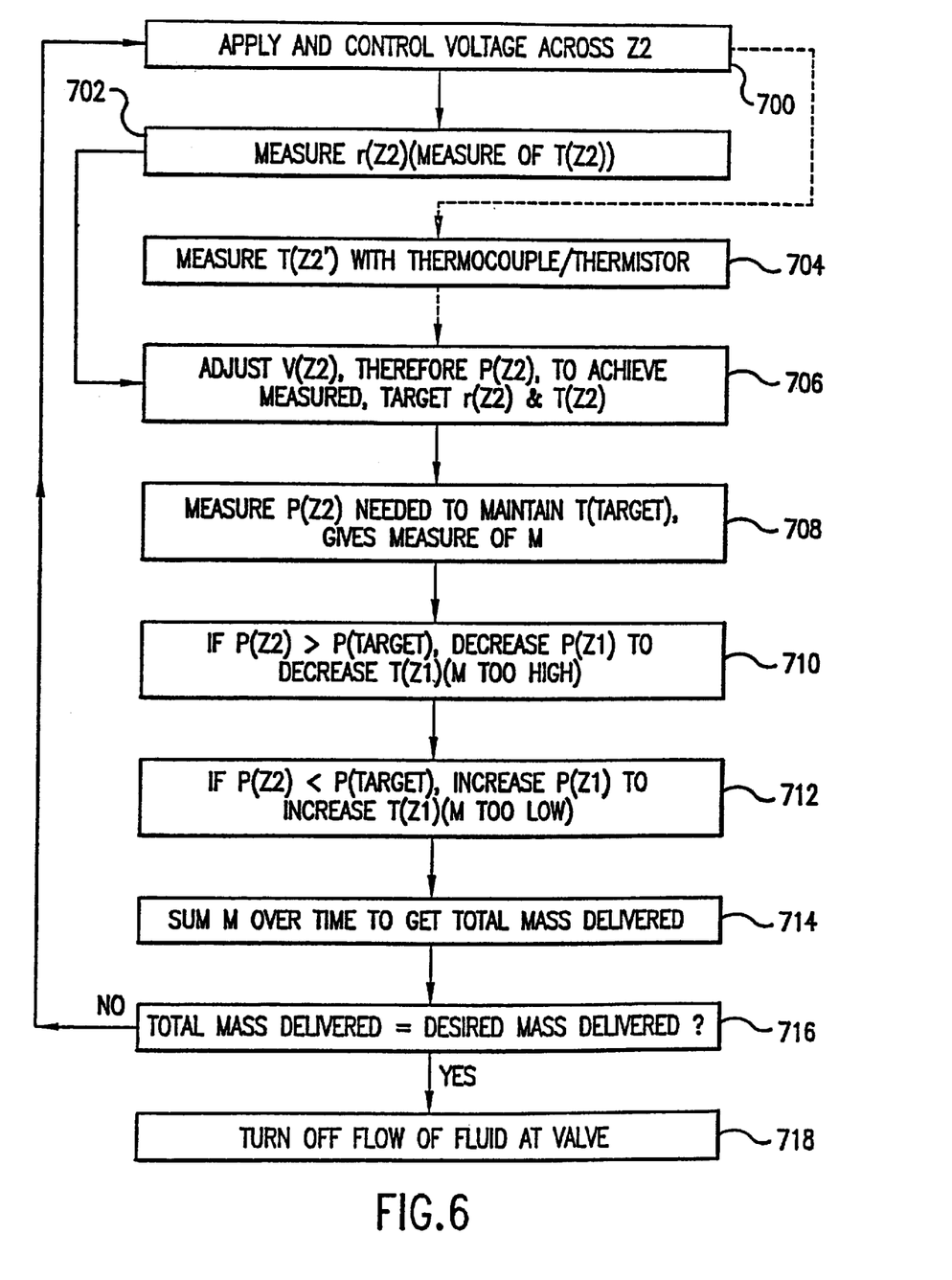
FIG. 6 schematically illustrates an exemplary control scheme for a CAG in accordance with the present invention.
Figure 7:
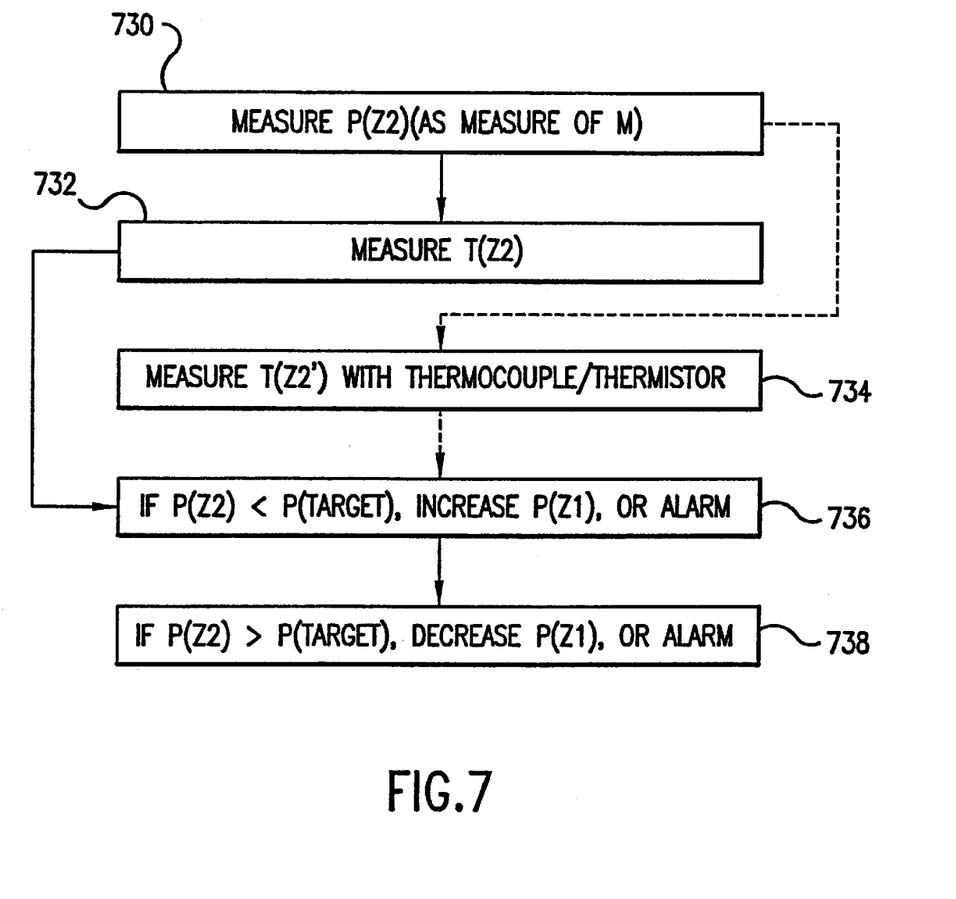
FIG. 7 schematically illustrates another exemplary control scheme for a CAG in accordance with the present invention.

FIG. 6 schematically illustrates a control scheme for controller 608 which assists in determining if a fault condition exists in the CAG. The control scheme illustrated in FIG. 6 can be integrated into the control scheme illustrated in FIG. 5 and described with reference thereto, or can precede or follow the control scheme of FIG. 5. In step 730, the power consumed in zone Z2 is measured, which is a measure of the mass flow rate through zone Z2. The temperature of zone Z2 is then measured in step 732, either by measuring the resistance of the heater element in zone Z2, or by measuring the temperature T(Z2') at the thermocouple as at step 734.

At step 736, the controller determines whether the power consumption measured at zone Z2 is less than P(target), and the controller increases the voltage across (and therefore the power consumed by) zone Z1, to increase the mass flow rate M. However, this action may fail to increase P(Z2) to P(target). A power consumption measurement which is low for the temperature measured can be indicative of a blockage in the flow passage of the CAG, which would lower the mass flow rate and the power P(Z2) required to achieve the target T(Z2). In this event, an alarm could be sounded, and the apparatus shut down.

At step 738, the controller determines whether the power consumption measured at zone Z2 is greater than P(target), and the controller decreases the voltage across (and therefore the power consumed by) zone Z1, to decrease the mass flow rate M. However, this action may fail to decrease P(Z2) to P(target). A power consumption measurement which is high for the temperature measured can be indicative of an overflow condition in the flow passages of the CAG, which would raise the mass flow rate and the power P(Z2) required to achieve the target T(Z2). In this event, an alarm could be sounded, and the apparatus shut down.

According to the invention, a control algorithm can be used to maintain a downstream heater at a desired target resistance. Once steady state operation is achieved (e.g., in less than 100 msec), the algorithm can calculate the energy consumption (power) in the downstream heater based on an arbitrary time scan (e.g., 32 msec average). The frequency at which the upstream heater is pulsed can be adjusted up or down as a function of whether the downstream heater is operating at a desired target power. If the power in the downstream heater is below the target level, the time between the upstream heater pulses can be decreased to thereby increase the temperature in the upstream heater zone.

Figure 8:
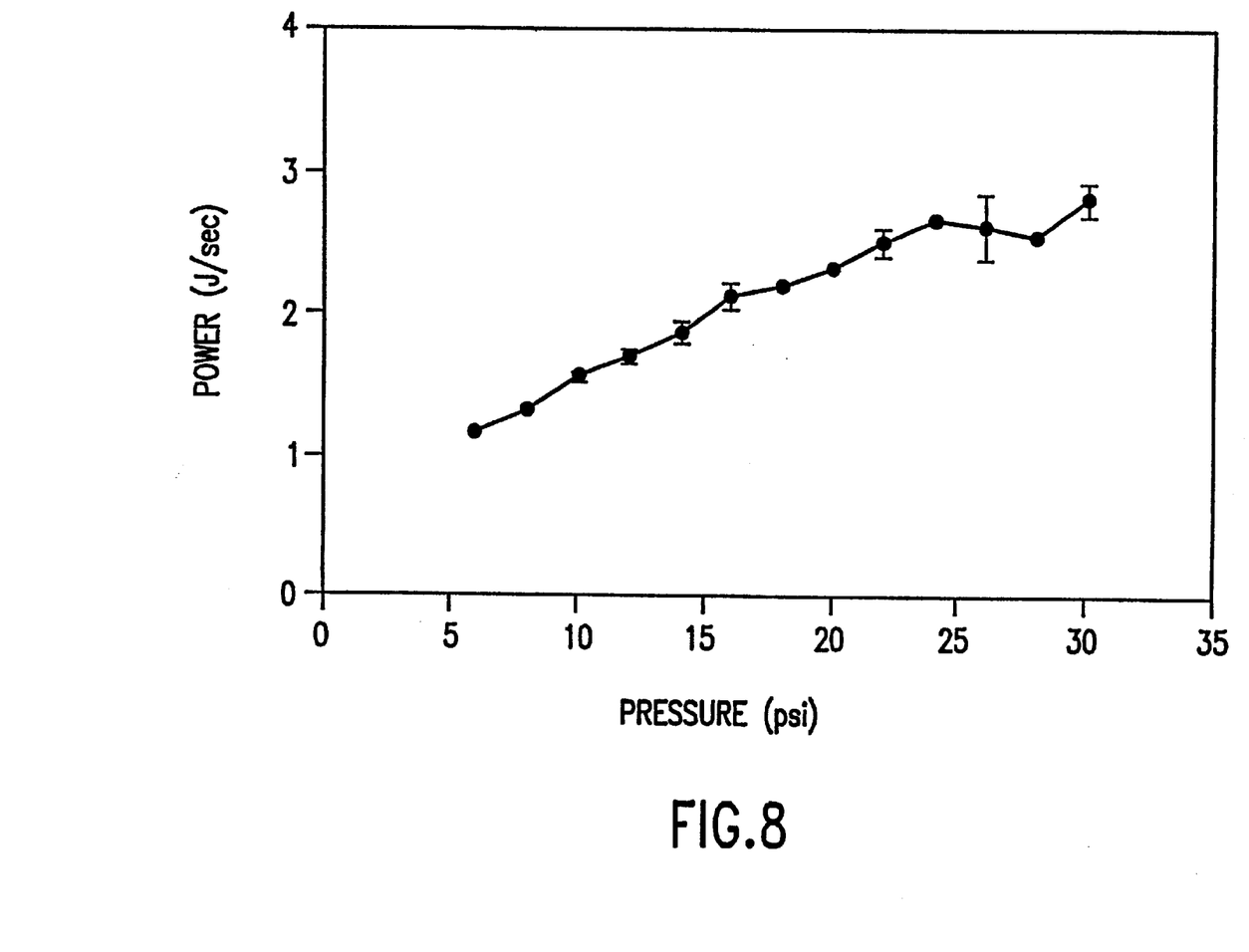
FIG. 8 is a graph of power as a function of feed pressure of propylene glycol.
Figure 9:
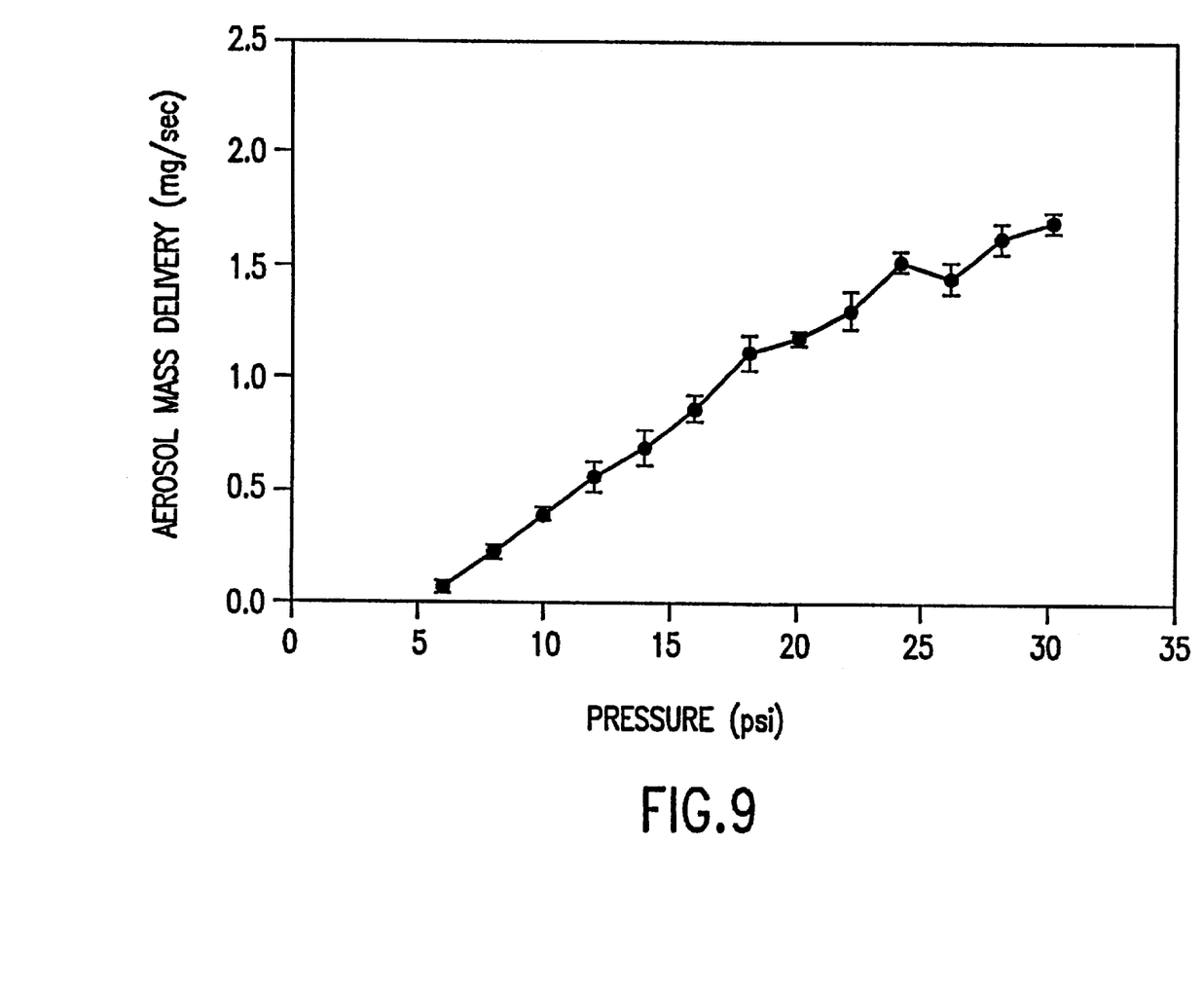
FIG. 9 is a graph of aerosol mass delivery for propylene glycol in a single heating zone as a function of feed pressure of propylene glycol.

Experiments in which energy consumption and mass delivery are compared as a function of feed pressure are shown in FIGS. 8 and 9 wherein FIG. 8 shows power as a function of feed pressure of propylene glycol in the case where the upstream heater is turned off, the run time is 10 seconds and the downstream resistance target is 0.36 ohms. FIG. 9 shows aerosol mass delivery under the same conditions as used in FIG. 8. Thus, FIGS. 8 and 9 show typical one heating zone response to increasing feed pressure. As shown, the power usage and aerosol mass increase in a linear fashion with increasing pressure.

Figure 10:
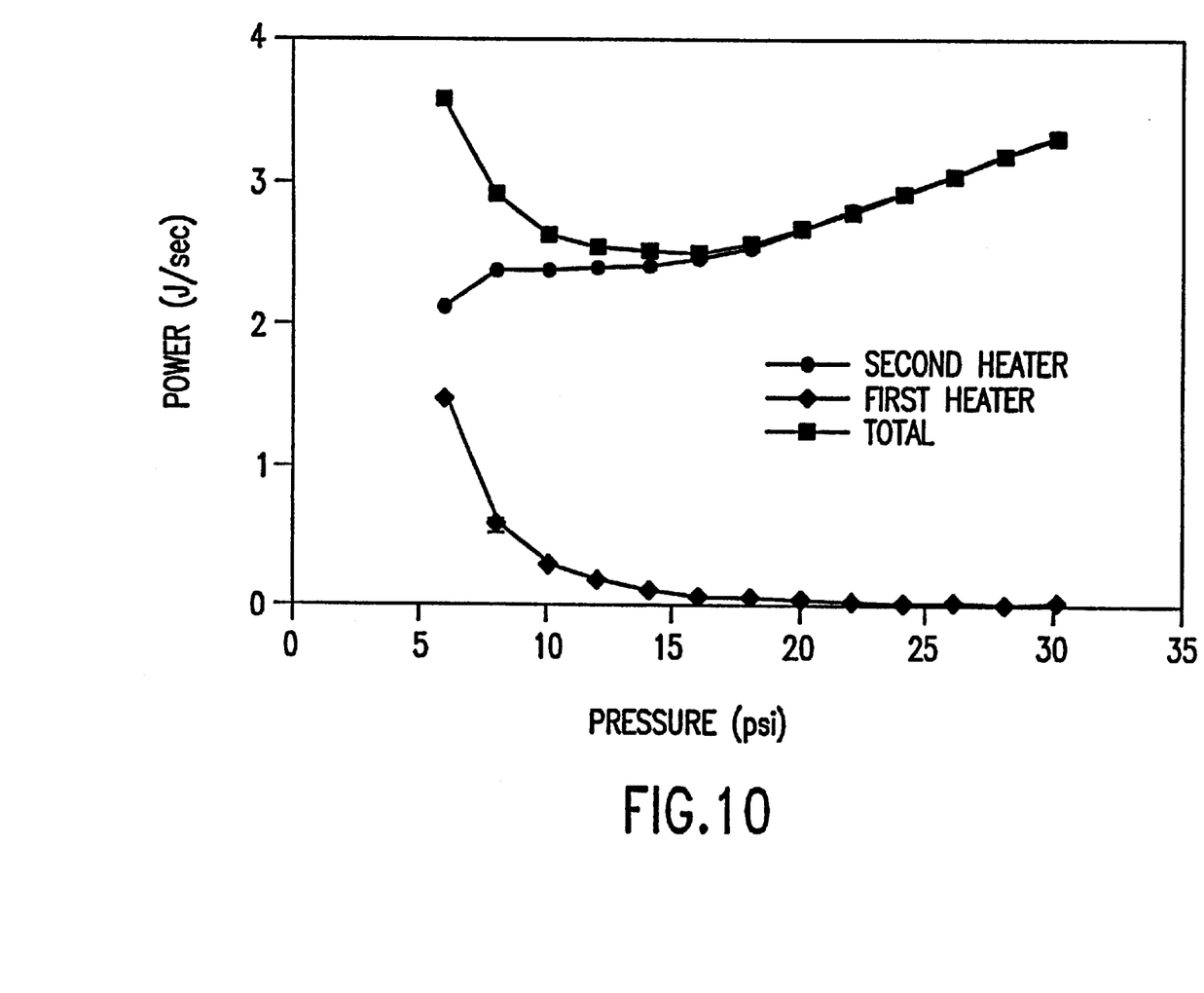
FIG. 10 is a graph of power as a function of feed pressure for a downstream heater, upstream heater and both heaters.

In two-zone experiments, the downstream heater target power level was 2.6 watts, the upstream heater was turned off, and the feed pressure was 20 psi. The initial setting for the upstream heater was to supply power to the upstream heater once every 8 msec. Further, pressure was varied from 6 to 30 psi and the energy usage and mass deliveries were measured. FIG. 10 shows power curves as a function of pressure for the downstream heater, the upstream heater and both heaters, the downstream heater target resistance being set at 0.36 ohms, the downstream heater target power being set at 2.6 watts and the fluid being propylene glycol.

Figure 11:
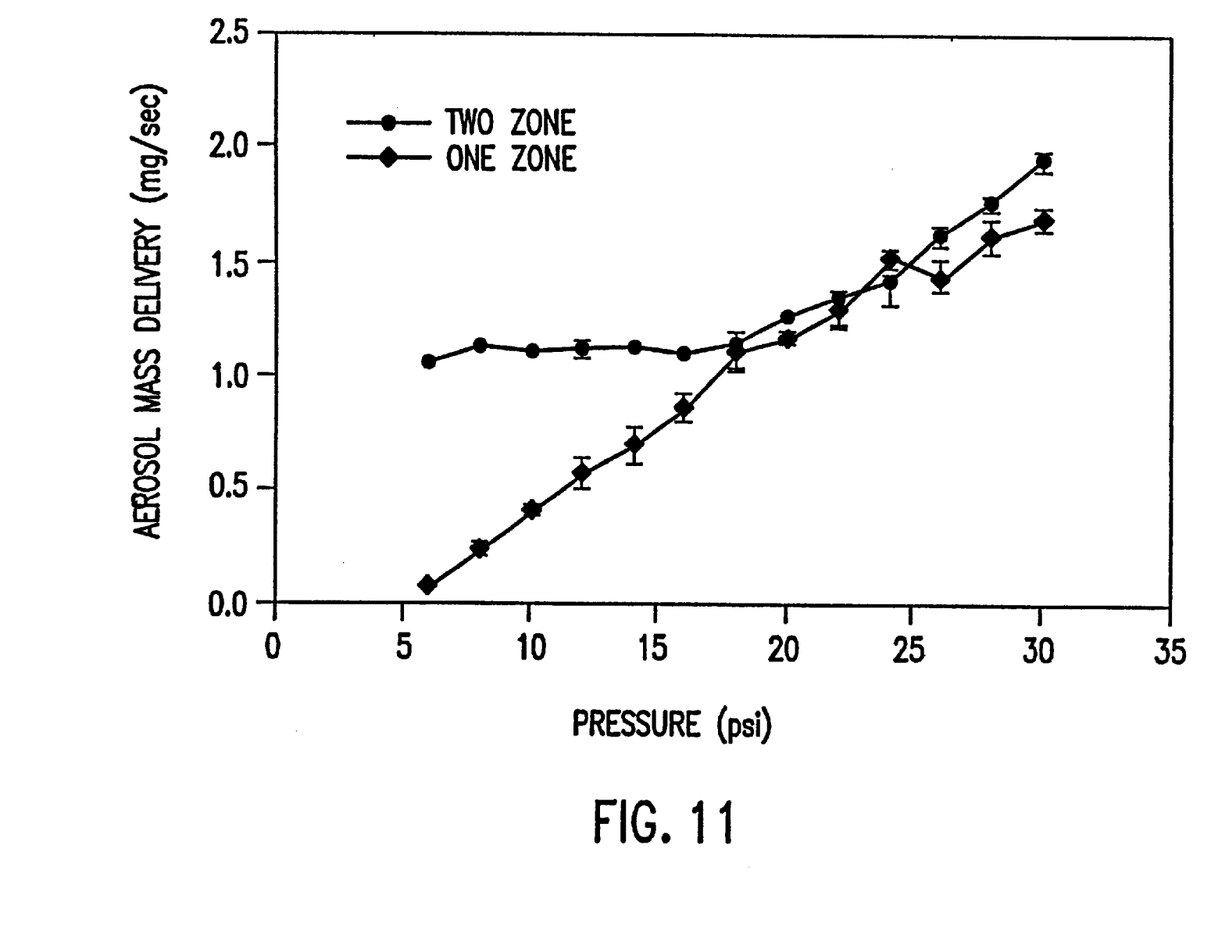
FIG. 11 is a graph of aerosol mass delivery for propylene glycol in a two zone heater as a function of feed pressure of propylene glycol.

FIG. 11 shows the aerosol mass delivery for propylene glycol (PG) in a two-zone heater wherein the run time was 10 seconds, the downstream heater target resistance was 0.36 ohms, the upstream heater firing frequency was once every 8 msec and the downstream heater target power was 2.6 watts. Results for one-zone heating was added to FIG. 11 for comparison. As shown, the aerosol mass delivery for the two-zone heating arrangement remains relatively constant over the feed pressure range of 6 to 20 psi. Above 20 psi, the aerosol mass delivery tracks the one-zone data because the target power level was set for the 20 psi case and the upstream heater is unable to cool the PG to compensate for an increase in pressure above this target. Accordingly, heating the PG to reduce its viscosity and increase its flow rate can be used to compensate for pressure variations and/or temperature variations. Moreover, these experiments demonstrate that power consumption of the downstream heater can be used as a feedback signal to control the upstream heater power. In the case illustrated in FIG. 11, a 32 msec power average was used for the downstream heater and the heating arrangement responded rapidly to achieve the desired targets.

While the invention has been described in detail with reference to preferred embodiments thereof, it will be apparent to one skilled in the art that various changes can be made, and equivalents employed, without departing from the scope of the invention.

What is claimed is:

1. A capillary aerosol generator comprising:
   a flow passage having an inlet and an outlet;
   a heater in heat transfer communication with the flow passage wherein the heater comprises a capillary; and
   a controller in electrical communication with the heater, the controller being operable to monitor power consumed by the heater and automatically supply power to the heater as a function of the consumed power provided to said controller as a feedback signal to achieve a target temperature sufficient to volatilize a liquid passing through said flow passage.

2. A capillary aerosol generator according to claim 1, wherein the controller selectively supplies a constant voltage across the heater.

3. A capillary aerosol generator according to claim 1, wherein the controller selectively measures the resistance of the heater.

4. A capillary aerosol generator according to claim 1, wherein the controller selectively measures the voltage across the heater.

5. A capillary aerosol generator according to claim 1, wherein the controller comprises a memory including an instruction set which instructs the controller when to measure resistance and/or voltage, and when to apply voltage to the heater.

6. A capillary aerosol generator according to claim 1, further comprising a temperature sensor in heat transfer communication with the flow passage.

7. A system useful for generating an aerosol, comprising:
a capillary aerosol generator according to claim 1,
a source of pressurized fluid; and
a valve between the source of pressurized fluid and the capillary aerosol generator.

8. A system according to claim 7, wherein the valve is an automatically controllable valve, the controller being operable to selectively open and close the valve.

9. A process of forming an aerosol from a liquid, comprising the steps of:
supplying liquid to an upstream end of a flow passage of an aerosol generator including a heater positioned in heat transfer communication with the flow passage, wherein the heater comprises a capillary;
measuring power consumed by the heater;
controlling the temperature of the heater as a function of the consumed power with a controller using the consumed power as a feedback signal; and
heating the liquid such that the liquid is volatilized and exits from a downstream end of the flow passage.

10. A process of forming an aerosol according to claim 9, further comprising adjusting a voltage across the heater based on the measured parameter.

11. A process of forming an aerosol according to claim 10, comprising comparing the power consumed in maintaining the temperature of the heater at a predetermined temperature (P(Z2)) to a target power level (P(Target));
decreasing the power applied to the heater if (P(Z2))>(P(Target)); and
increasing the power applied to the heater if (P(Z2))<(P(Target)).

12. A capillary aerosol generator for generating an aerosol by vaporizing a liquid comprising:
a capillary flow passage having an inlet and an outlet;
a liquid source in fluid communication with the inlet;
a resistance heater in heat transfer communication with a liquid vaporization zone of the flow passage; and
a controller in electrical communication with the heater, the controller being operable to monitor power consumed by the heater and selectively meter power to the heater as a function of said monitored consumed power provided as a feedback signal to said controller to achieve a target temperature.

13. A capillary aerosol generator according to claim 12, further comprising a valve controlling flow of liquid from the liquid source to the flow passage, the controller communicating with the valve to control operation thereof.

14. A capillary aerosol generator according to claim 12, wherein the aerosol generator comprises an inhaler having a mouthpiece.

15. A capillary aerosol generator according to claim 12, wherein the flow passage extends through a capillary tube of resistance heating material and the heater comprises a section of the capillary tube.

16. A capillary aerosol generator according to claim 12, wherein the flow passage extends through a capillary tube and the heater comprises an external or internal heater which heats the capillary tube.

17. A capillary aerosol generator according to claim 12, further comprising a temperature sensor in heat transfer communication with a distal end of the flow passage.

18. A process of forming an aerosol from a liquid, comprising the steps of:
supplying liquid to an upstream end of a capillary flow passage of an aerosol generator including a heater positioned in heat transfer communication with the flow passage;
measuring power consumed by the heater;
controlling the temperature of the heater based on the consumed power with a controller using the consumed power as a feedback signal; and
heating the liquid such that the liquid is volatilized and exits from a downstream end of the flow passage and forms an aerosol.

19. A process of forming an aerosol according to claim 18, further comprising calculating mass flow of the liquid through the flow passage as a function of power consumed by the heater.

20. A process of forming an aerosol according to claim 10, wherein the liquid comprises propylene glycol and the heating vaporizes the propylene glycol to produce the aerosol.

* * * * *